United States Patent [19]

Gombrich et al.

[11] Patent Number: 5,607,860
[45] Date of Patent: Mar. 4, 1997

[54] DUAL CHAMBER BLOOD CULTURE BOTTLE

[75] Inventors: Peter P. Gombrich, Chicago; Richard A. Domanik, Libertyville; William J. Mayer, South Barrington, all of Ill.

[73] Assignee: Accumed, Inc., Chicago, Ill.

[21] Appl. No.: 477,657

[22] Filed: Jun. 7, 1995

[51] Int. Cl.$^6$ ..................................... C12M 3/00
[52] U.S. Cl. ........................... 435/287.3; 435/287.4; 435/287.6; 435/289.1; 435/303.1; 435/303.2; 435/304.2
[58] Field of Search .................. 435/287.3, 287.4, 435/287.5, 287.6, 289.1, 303.1, 303.2, 304.2

[56] References Cited

U.S. PATENT DOCUMENTS

| | | | |
|---|---|---|---|
| 3,730,170 | 5/1973 | Michael | 128/2 F |
| 4,010,078 | 3/1977 | Taylor | 195/139 |
| 4,136,680 | 1/1979 | Southworth | 128/213 |
| 4,256,461 | 3/1981 | Wallace et al. | 23/230 B |
| 4,435,505 | 3/1984 | Zierdt | 435/34 |
| 4,576,173 | 3/1986 | Parker et al. | 128/633 |
| 4,772,558 | 9/1988 | Hammann | 435/300 |
| 4,810,651 | 3/1989 | Schwartz | 435/296 |
| 4,874,707 | 10/1989 | Bock | 435/253.6 |
| 4,952,498 | 8/1990 | Waters | 435/34 |
| 5,051,360 | 9/1991 | Waters | 435/34 |
| 5,116,506 | 5/1992 | Williamson et al. | 210/610 |
| 5,262,326 | 4/1993 | Jaeger et al. | 435/300 |
| 5,290,701 | 3/1994 | Wilkins | 435/312 |
| 5,336,600 | 8/1994 | Monget | 435/34 |
| 5,364,642 | 11/1994 | Altura et al. | 426/74 |
| 5,403,741 | 4/1995 | Holbrook | 435/291 |

FOREIGN PATENT DOCUMENTS 60-5295  11/1985  Japan .

OTHER PUBLICATIONS

PCT/FR93/00062, published on Aug. 5, 1993 as WO93/15183.
PCT/EP87/00538, published on Apr. 7, 1988 as WO88/02397.

*Primary Examiner*—David A. Redding
*Attorney, Agent, or Firm*—Banner & Witcoff, Ltd.

[57] ABSTRACT

A multi-chambered blood culture device for simultaneously conducting two blood culture tests on a single blood sample. An integrated unit is provided for receiving a blood sample simultaneously into two independent sample vials. Independent culture chambers contain growth media, one culture chamber preferably containing an aerobic growth medium and another culture chamber preferably containing an anaerobic growth medium. The device is configured to isolate the sample vials and culture chambers from contaminants of the external environment. Further, means are provided for releasing the blood from one sample vial into one culture chamber while simultaneously releasing the blood from the other sample vial into the other culture chamber. In the preferred embodiment, outer walls of the device are constructed of transparent plastic so as to enable visual observance of microorganism growth in the respective culture chambers.

26 Claims, 15 Drawing Sheets

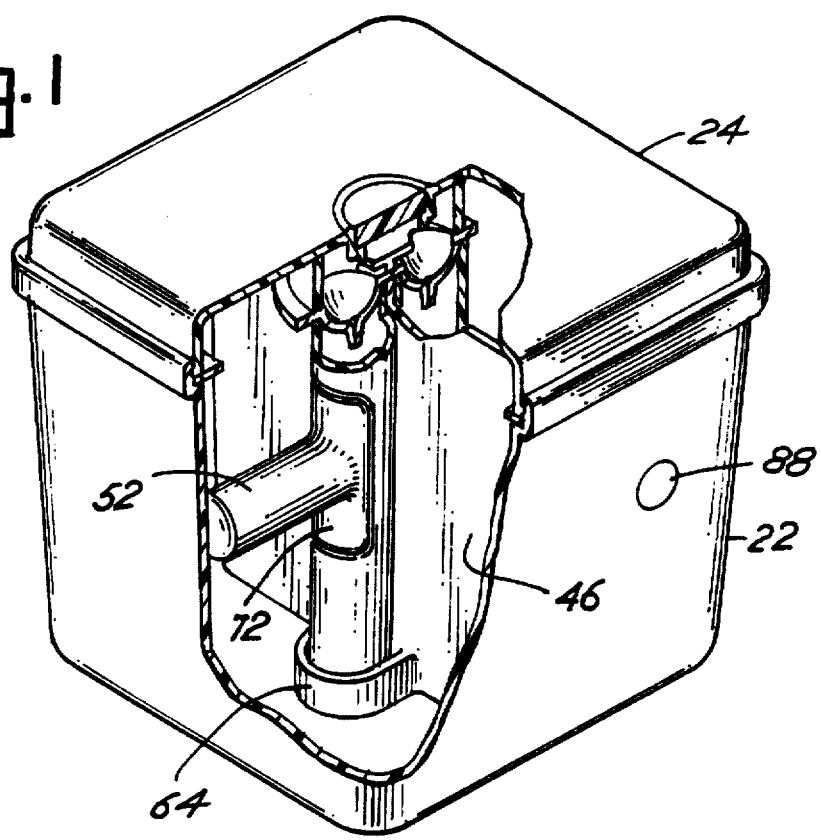
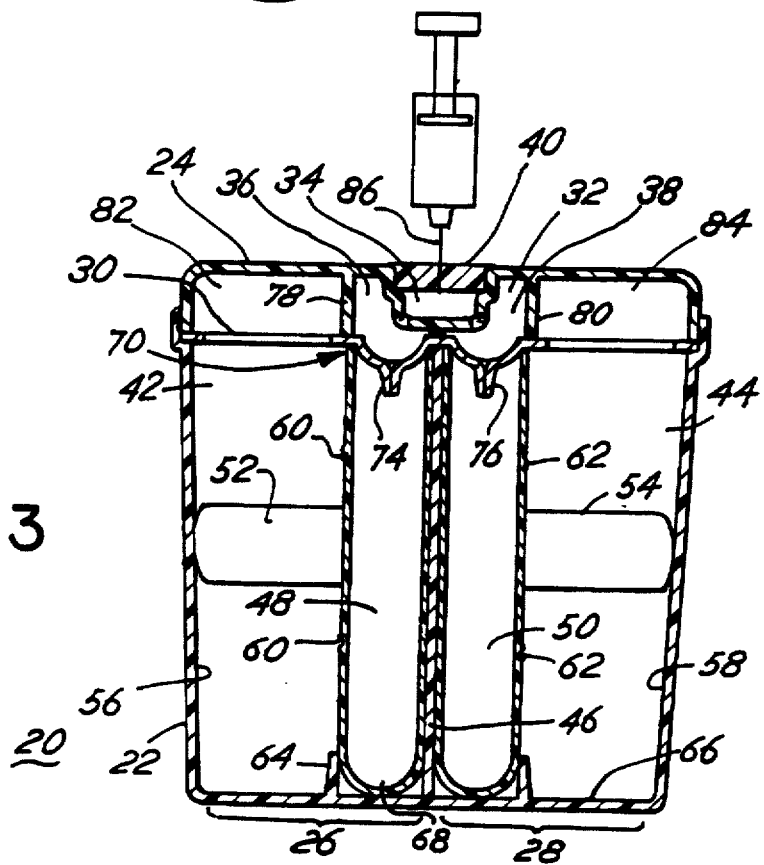

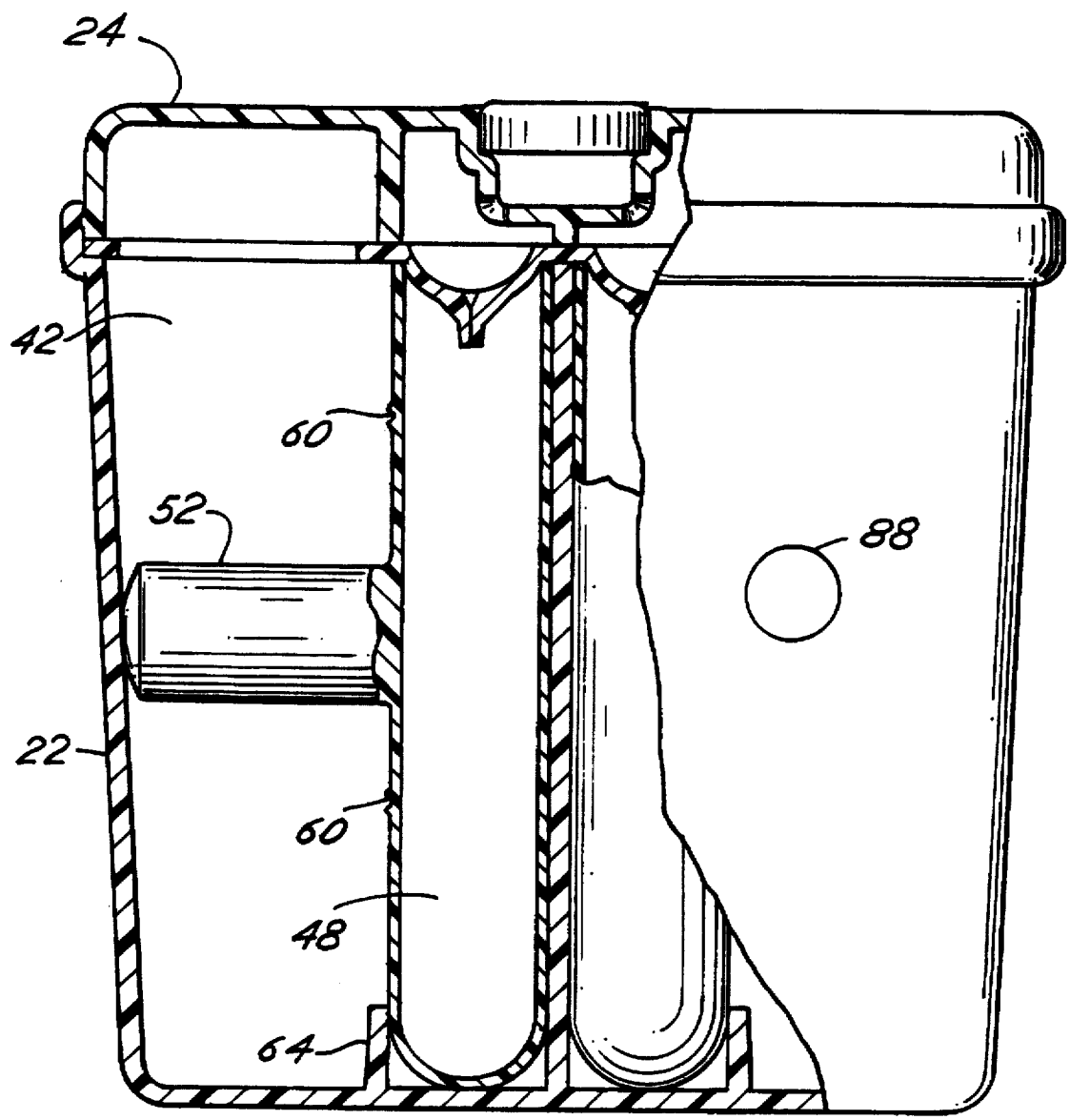

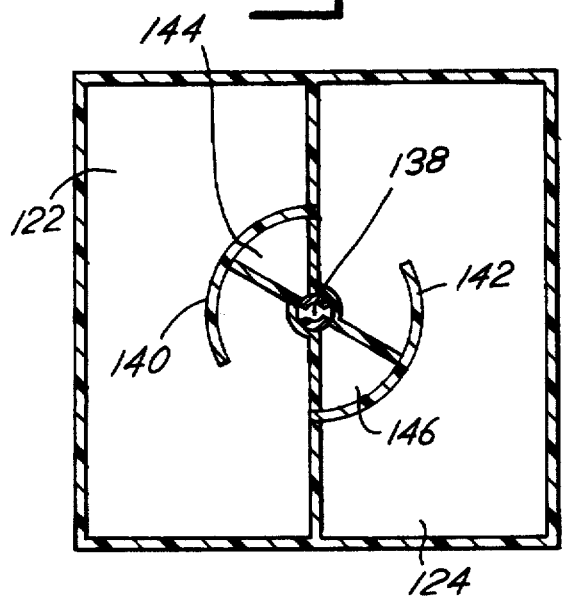
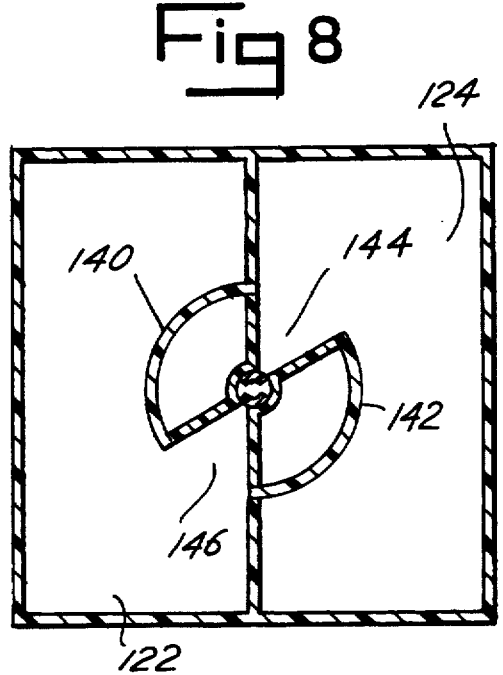
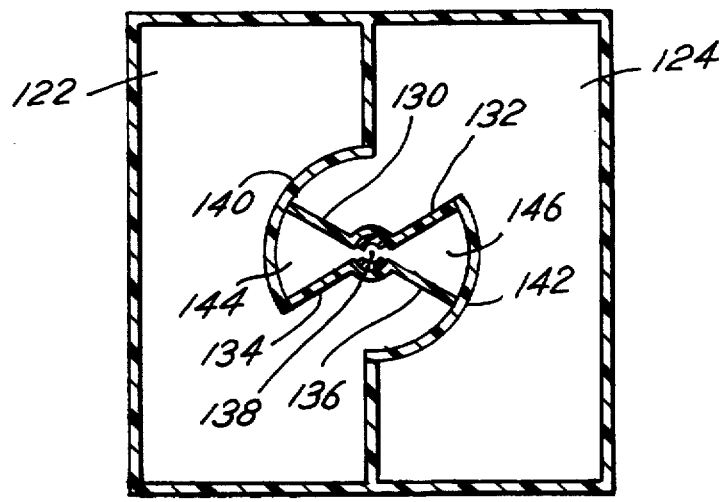

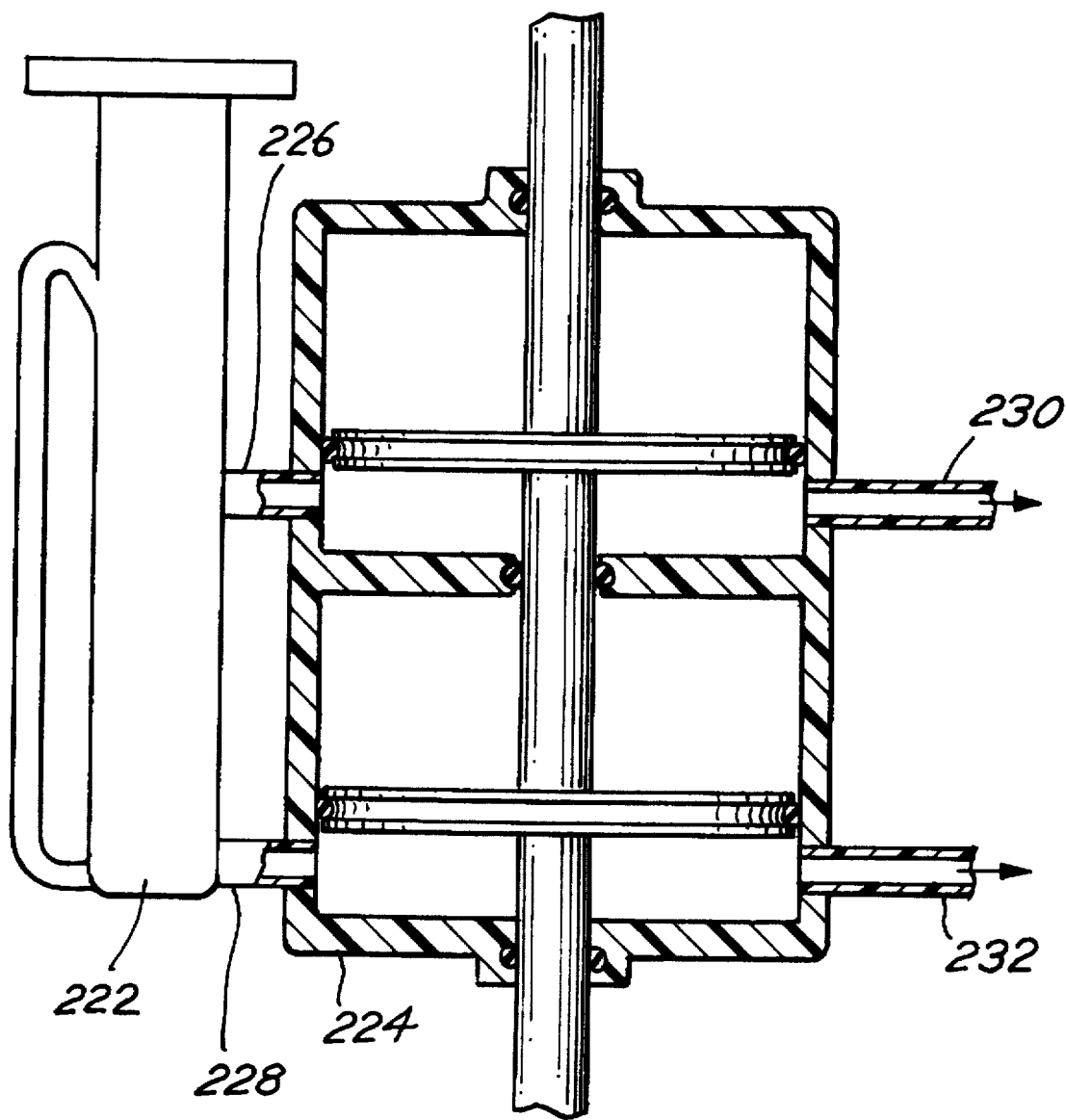

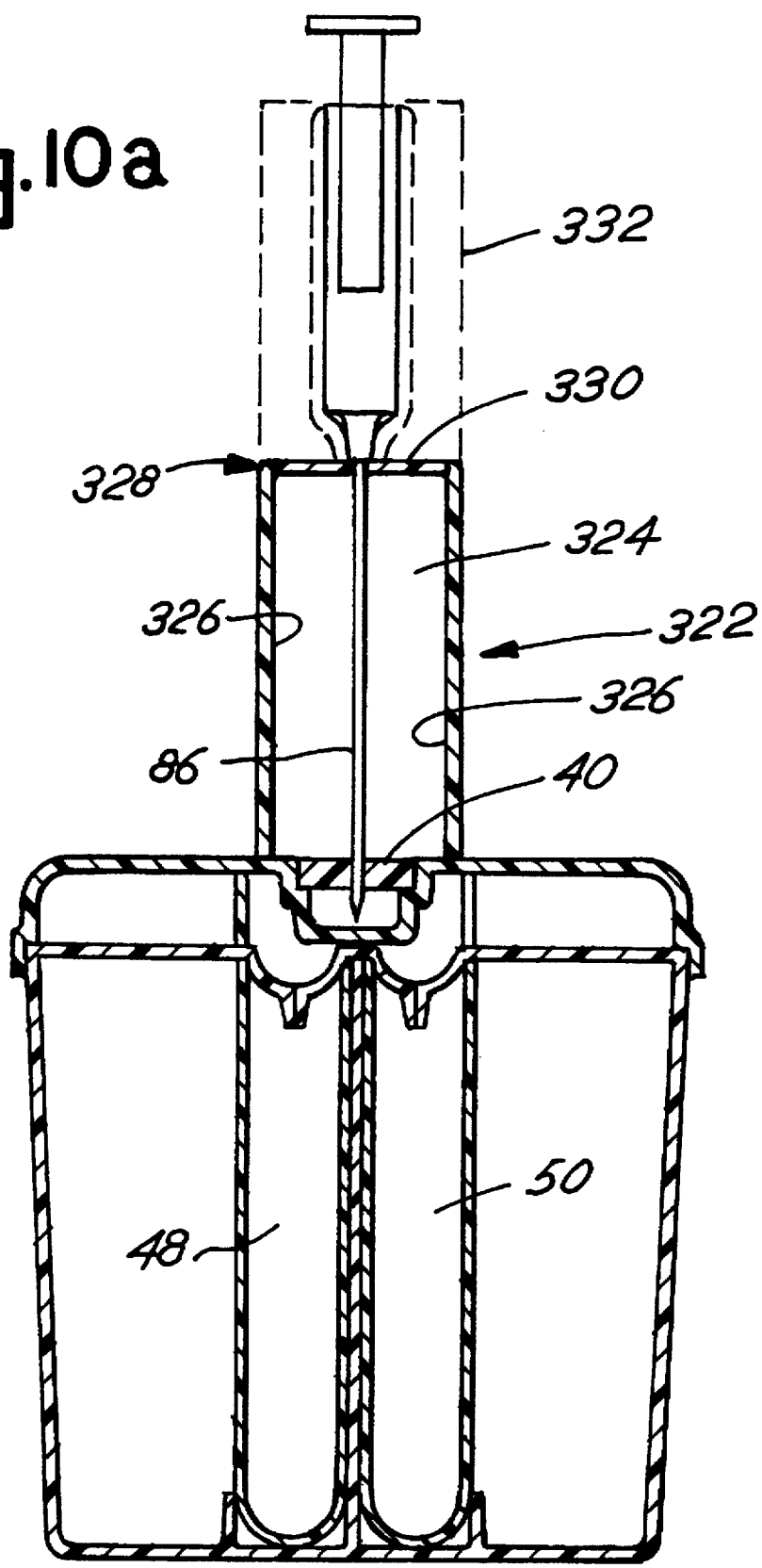

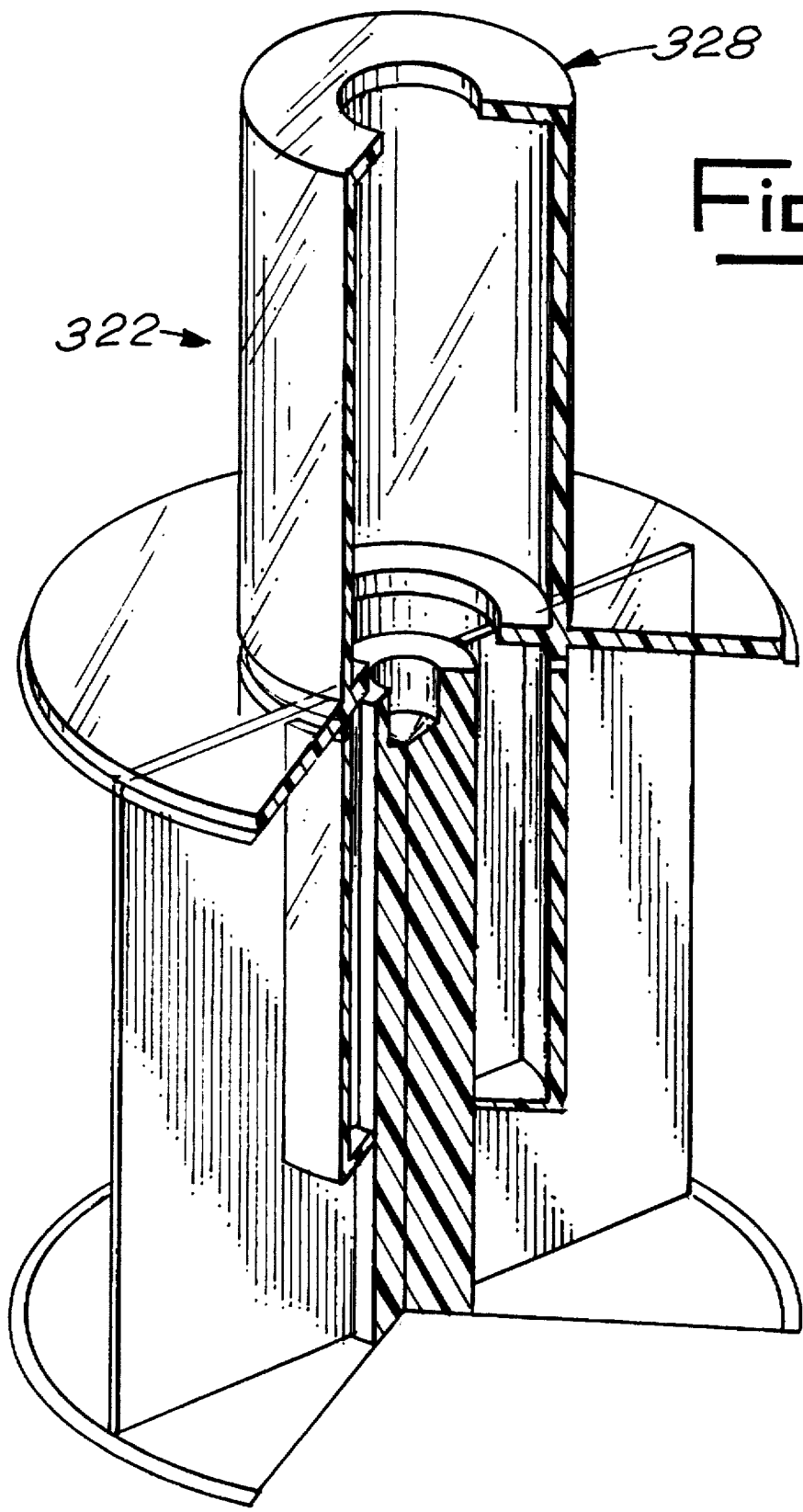

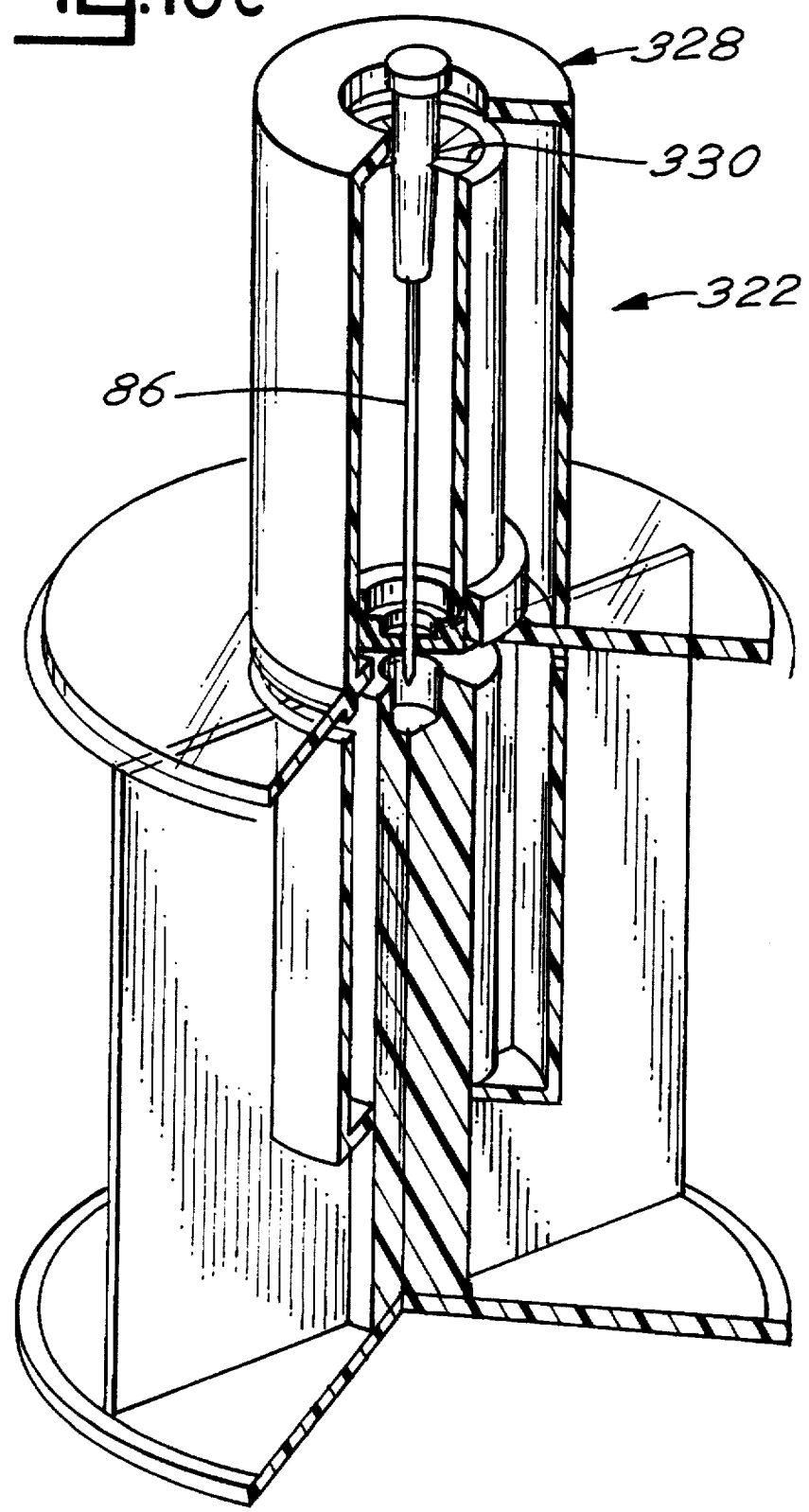

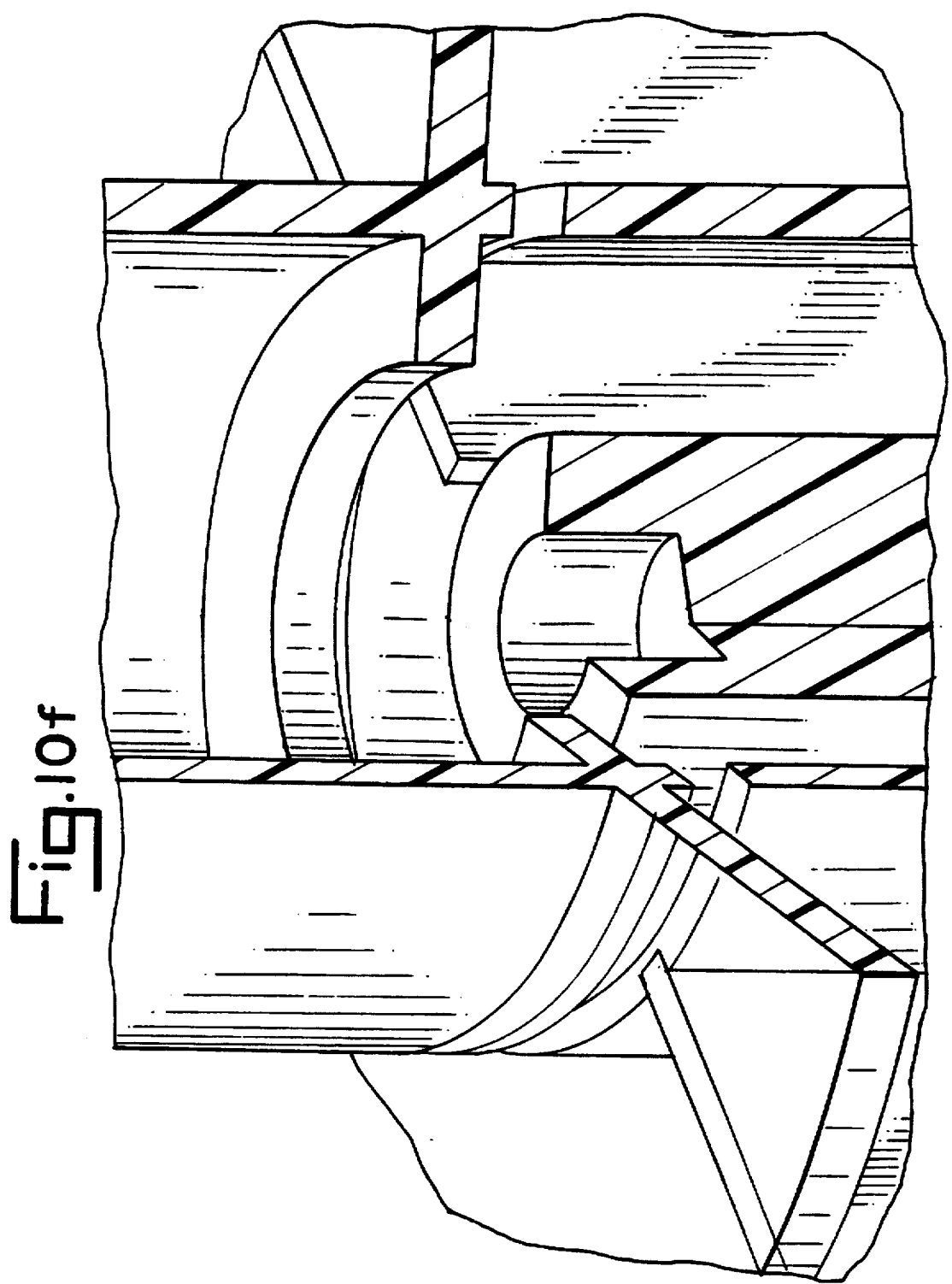

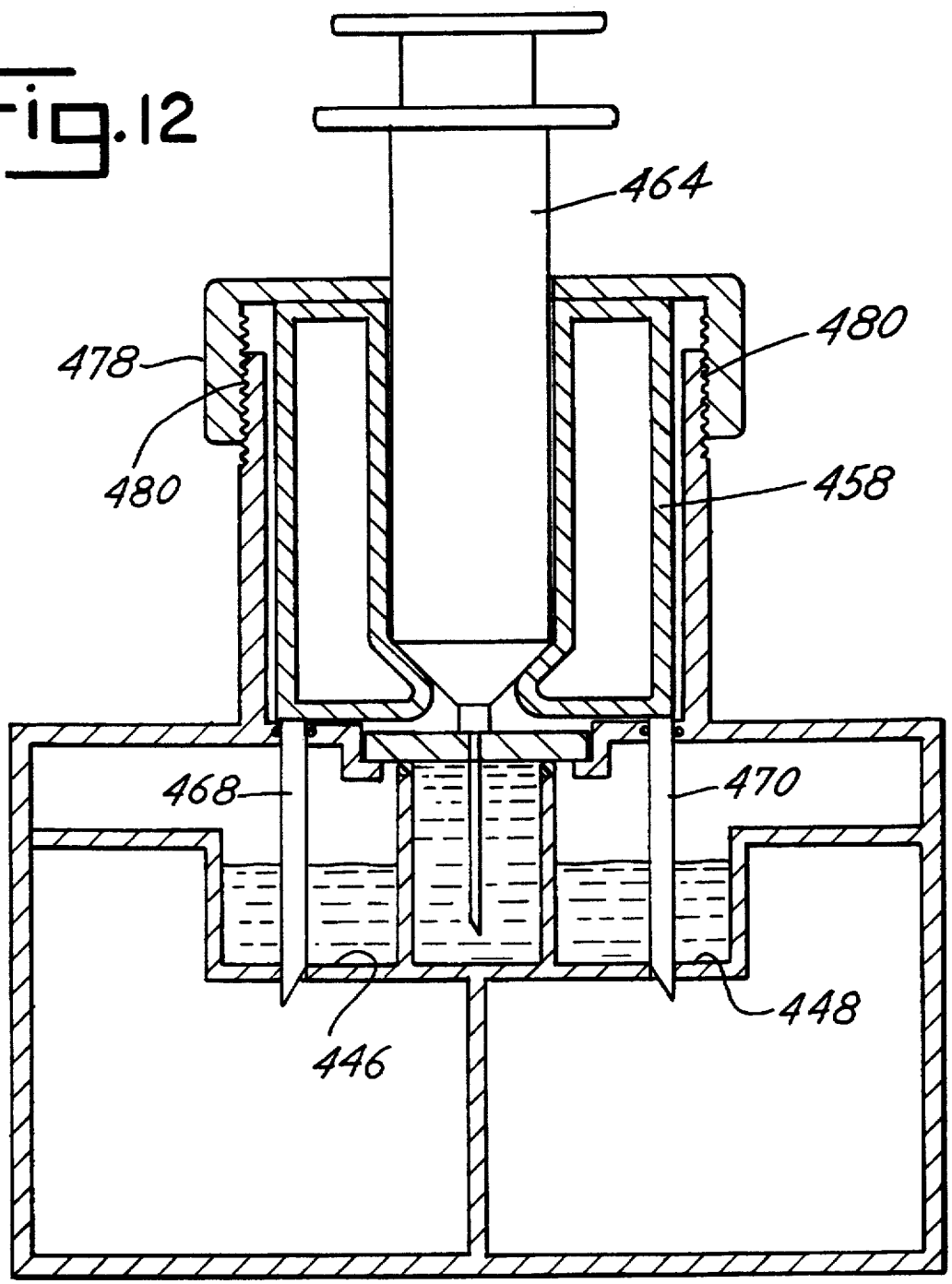

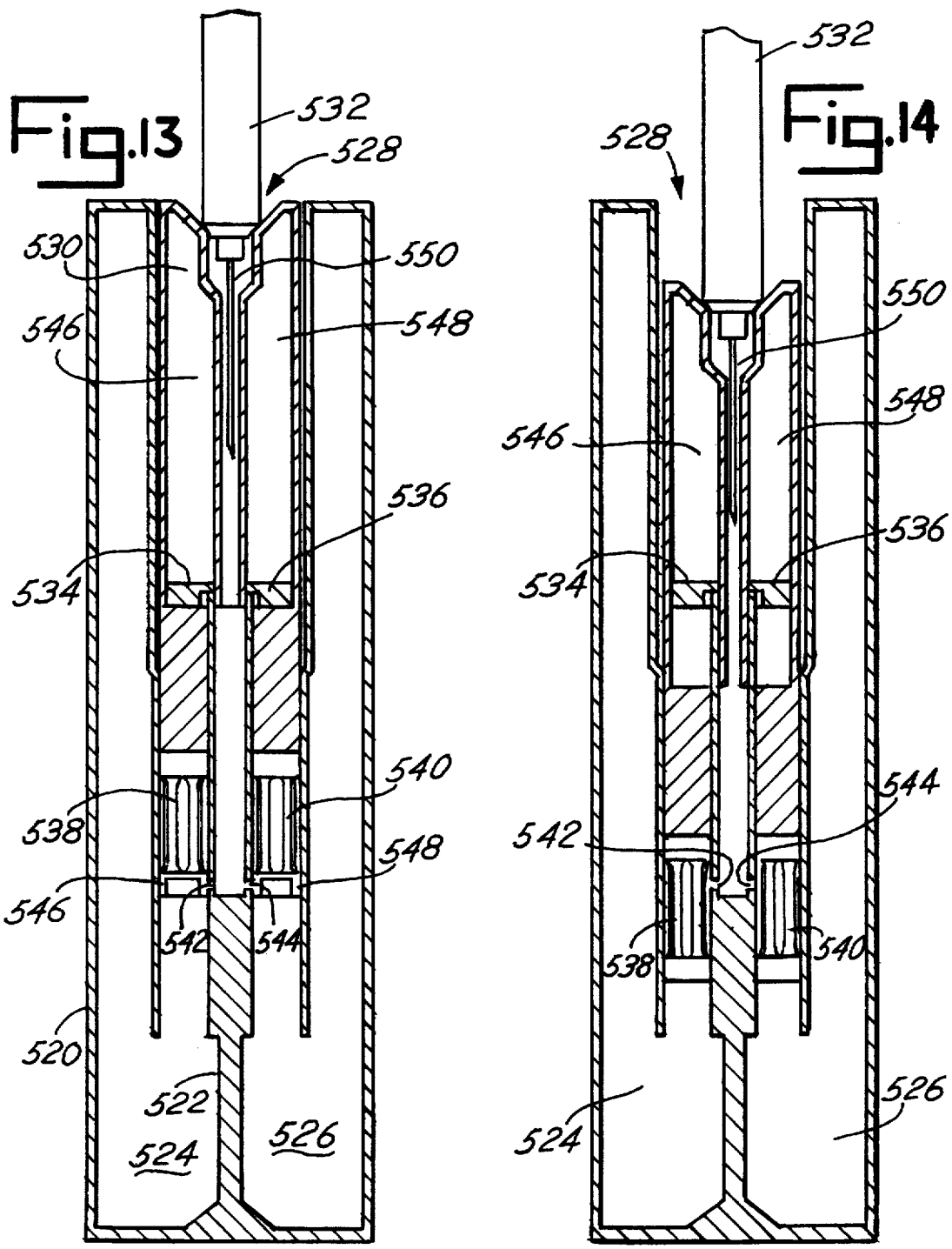

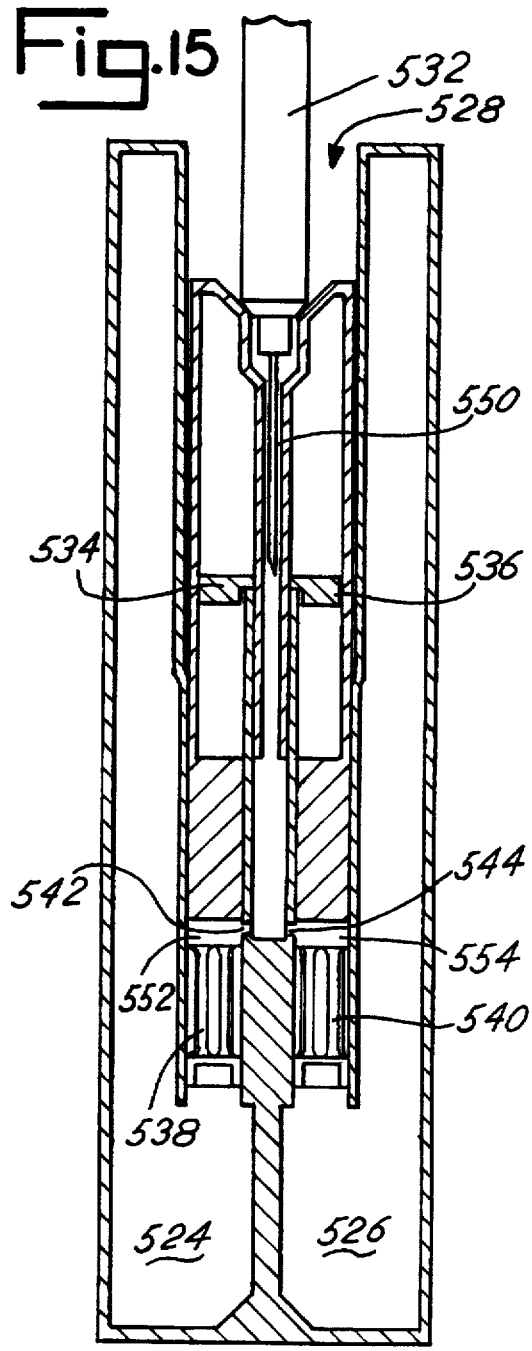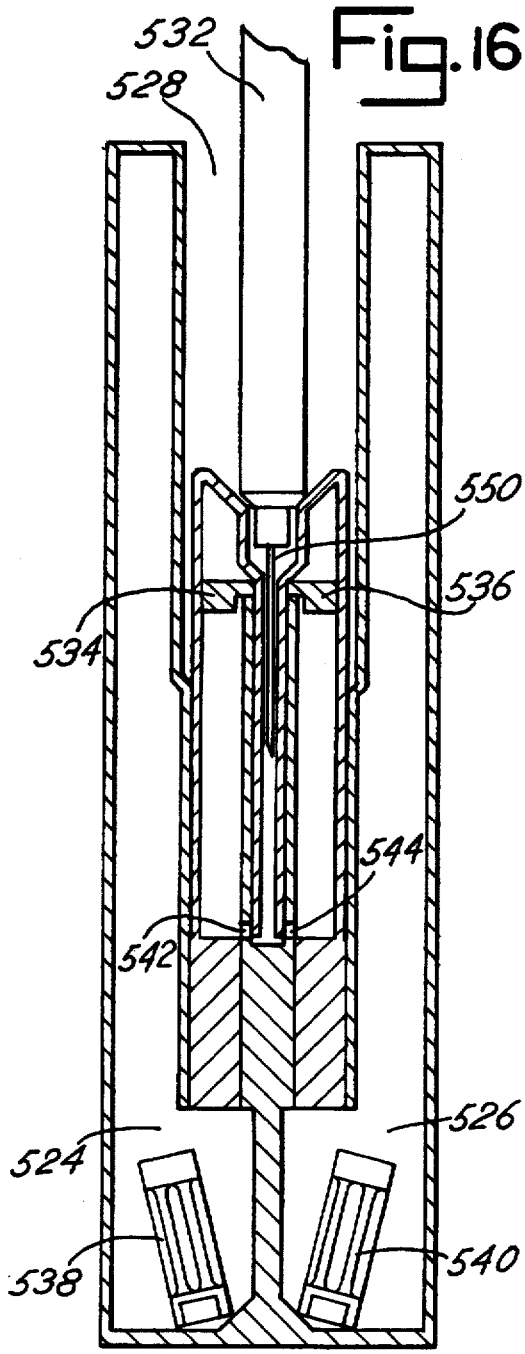

DUAL CHAMBER BLOOD CULTURE BOTTLE

BACKGROUND OF THE INVENTION

This application is filed contemporaneously with three other U.S. patent applications, entitled respectively "Dual Chamber Culture Bottle with Rotating Inlet Valve Assembly," application Ser. No. 08/475,380; "Dual Chamber Blood Culture Bottle with Break Seal," application Ser. No. 08/477,656; and "Dual Chamber Blood Culture Bottle with Syringe Capture and Piston Assembly," application Ser. No. 08/477,655; each by the same inventors as the present application, and each assigned to the owner of the present application.

The present invention relates generally to blood culture bottles and more particularly to a multi-chambered blood culture apparatus that may simultaneously perform a plurality of different tests on a sample of blood. Blood culture tests are typically performed to diagnose certain types of systemic infections present in the blood of a patient. In such a test, a sample of blood is first extracted from a patient, typically with a hypodermic syringe. The blood sample is then combined with a sterile nutrient growth medium and incubated under defined conditions for a period of time ranging from hours to weeks in order to encourage the growth of any blood-borne pathogens that may be present. Because human blood is normally sterile, and assuming that proper aseptic technique is practiced in the collection of the specimen and the performance of the test, no microbial growth will be observed in the absence of infection. If an infection is present, however, microbial growth will occur and may be detected by any number of well known methods, including light scattering, optical absorbance, fluorescence and pressure change.

The selection of the growth medium and incubation conditions employed determines the types of microorganisms that are most likely to grow during a given test. In most cases of suspected infection, the type of infecting microorganism is not known. In such cases, it is common practice to prepare two blood specimens from the given patient and to perform separate blood culture tests on the two specimens. Usually, one of the specimens is tested in a blood culture bottle containing an aerobic growth environment, while the other specimen is tested in a blood culture bottle containing an anaerobic growth environment. This arrangement may enable a detection of microorganisms in the blood that thrive in an oxygen-rich environment, or, alternatively, microorganisms in the blood that thrive in an oxygen-poor environment. It is also common practice to repeat each of these tests so as to improve the probability of detecting a blood-borne infection. In addition, blood culture tests using varied growth media and incubation conditions may be employed in order to refine the initial diagnosis.

The performance of each blood culture test bears inherent costs. For instance, each blood culture test requires a specimen to be collected and transported in a suitable blood culture bottle to a laboratory. Growth media and ancillary materials must be obtained. The blood culture bottles must be prepared, and the specimens must be inoculated into the blood culture bottles. A suitable incubator must be provided, and the bottles containing specimens must be incubated under prescribed conditions for each given test. Microorganism growth must then be monitored during incubation. Finally, upon completion of the test, any contaminated materials that were generated, including the specimen collection and handling devices and the blood culture bottle, must be properly sterilized and disposed of. Each of these operations contributes to the cost of blood culture testing.

In addition, inherent risks are associated with every blood culture test. Each time an additional test is performed, the probability increases that a test bottle will be mislabeled, misdirected or improperly prepared, or that the test itself will be improperly performed or flawed. At best, such errors would necessitate repeating the test at an additional cost; at worst, such errors can result in an incorrect diagnosis for the patient. Risks are also present as a result of the frequent use of hypodermic syringes to collect blood specimens and inoculate the specimens into the blood culture bottles. The performance of each additional test increases the potential for accidental needle sticks, which, in the presence of any infectious microorganisms, may seriously infect the testing technician. In some cases, instead of using hypodermic syringes to inject the blood specimen into a sealed blood culture bottle, the blood specimen is pipetted into an open blood culture bottle and the bottle is then sealed. With this procedure, however, an increased risk exists that the bottle contents will inadvertently become contaminated and will yield erroneous diagnostic results.

In addition, blood culture bottles are traditionally made of glass and are therefore prone to break before, during and after use. While breakage before use merely increases costs, breakage during or after use presents a serious risk of infecting the testing technician. Additionally, in order to minimize the risk of contamination, blood culture bottles are usually sealed after being inoculated with a blood specimen. A sealed blood culture bottle is also required if a pressure sensor is used to detect microbial growth. However, certain specimens may generate enough pressure within the sealed bottle that the bottle may burst during incubation or the contents may spurt from the bottle when the seal is broken after testing. Both of these situations present an increased risk of infecting the technician with every additional blood culture test performed.

SUMMARY OF THE INVENTION

The object of the present invention is to reduce the costs and risks associated with typical blood culture testing. In principal aspect, the present invention is therefore a multi-chamber blood culture apparatus that enables simultaneous testing of a blood specimen under multiple different growth conditions. The invention includes at least one base cup including multiple base cup compartments. The base cup compartments are configured to hold predetermined separate portions of growth media as well as at least two sample containers. The base is configured such that blood from the sample containers can be selectively communicated to the base cup compartments to enable testing. The base cup compartments do not interconnect to one another, however, so that one compartment may include an aerobic blood culture media while another may include an anaerobic blood culture media. A plurality of tests may thus be conducted substantially simultaneously in the same integrated unit.

In another aspect, the present invention provides means for splitting a single blood specimen into multiple substantially identical aliquots, each suitable for performing a single blood culture test. Further, the present invention may provide means for capturing the specimen syringe so that the blood culture bottle and specimen syringe can be handled as a single unit during testing and disposal. Additionally, the apparatus of the present invention is preferably constructed of materials that minimize breakage, and the apparatus is configured so as to minimize adverse effects of increased internal pressure. Still further, the present invention provides means for permitting a noninvasive determination of the reaction process within a blood culture device, allowing for simultaneous application of readout techniques such as pressure change, fluorescence and optical absorbance.

The foregoing as well as other objects and features of the present invention are discussed or apparent in the following detailed description.

BRIEF DESCRIPTION OF THE DRAWINGS

Preferred embodiments of the present invention are described herein with reference to the drawings wherein:

FIG. 1 is an isometric view of an embodiment of the present invention;

FIG. 2 is a partial cross-sectional view of the device shown in FIG. 1;

FIG. 3 is a cross-sectional view of the device shown in FIG. 1;

FIG. 6 is a top cross-sectional view of the device shown in FIG. 4 in a loading position;

FIG. 7 is a top cross-sectional view of the device shown in FIG. 4 in a sealed position;

FIG. 8 is a top cross-sectional view of the device shown in FIG. 4 in a activation position;

FIG. 9 is a cross-sectional view of another alternative embodiment of the present invention;

FIGS. 10a–10f are views of other alternative embodiments of the present invention, including means for capturing a specimen syringe or needle;

FIG. 12 is a cross-sectional view of a modified version of the embodiment shown in FIG. 11;

FIG. 13 is a cross-sectional view of still another embodiment of the present invention, in an initial closed state;

FIG. 14 is a cross-sectional view of the embodiment shown in FIG. 13, in a filling state;

FIG. 15 is a cross-sectional view of the embodiment shown in FIG. 13, in a closed state; and FIG. 16 is a cross-sectional view of the embodiment shown in FIG. 13, in an activated state.

DETAILED DESCRIPTION OF THE PREFERRED EMBODIMENTS

Figure 4:
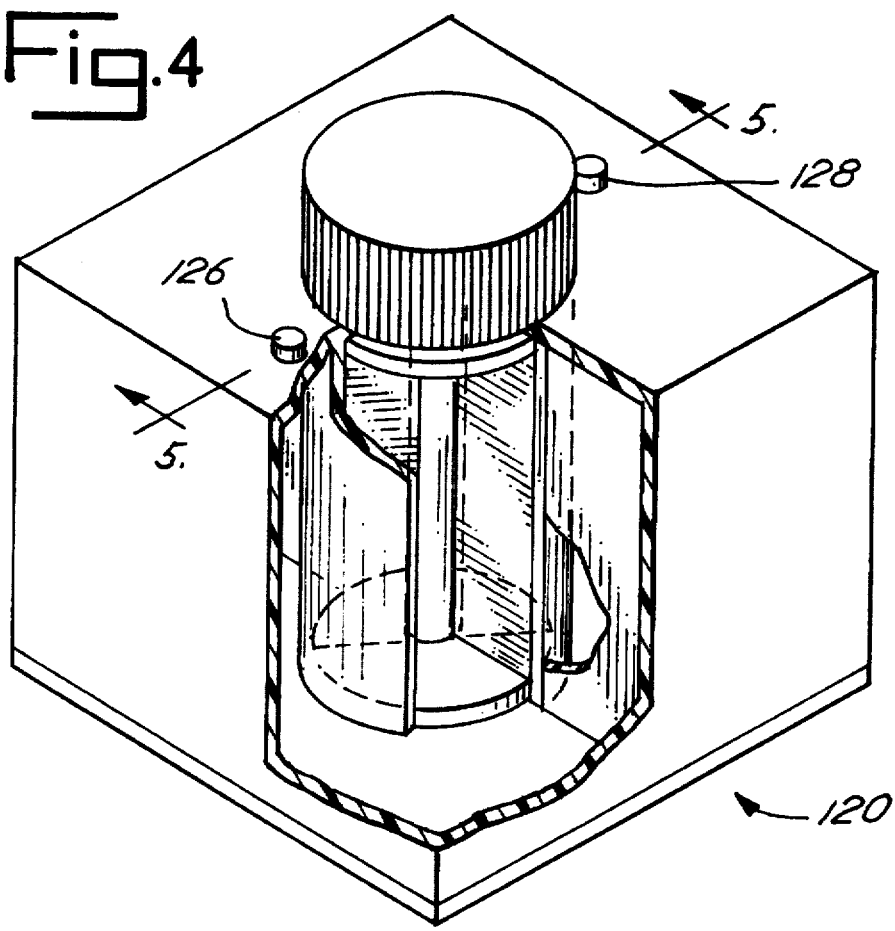
FIG. 4 is an isometric view of an alternative embodiment of the present invention.

Referring to FIGS. 1–3, the present invention is shown as a multi-chambered blood culture device 20. As illustrated, the device includes a base 22, a cap 24, first and second base cup compartments 26, 28, and a gasket 30. The cap or cover 24 includes a filler well 32 defining an aperture 34 and upper chambers 36, 38. The aperture 34 surrounds and includes a septum 40. The base cup compartments 26, 28 are integrally formed as part of the device to define culture chambers 42, 44, which are separated from one another by a central web 46. Included either inside or adjacent to the first and second chambers 42, 44 are, respectively, first and second sample containers or sample vials 48, 50 for holding blood. The sample vials 48, 50 are thus separated respectively into or about the first and second culture chambers 42, 44. Pins or fins 52, 54 project from each of the sample vials through the chambers 42, 46 and extend toward the outer walls or end walls 56, 58 of the respective chambers. A wall of each sample vial further defines breakaway portions 60, 62 adjacent to the pins.

The base 22 is a molded plastic part. Preferably, the base is approximately 3½" wide by 3" high by 1½ deep. The base has a central web 46 that divides the base into two independent compartments 42, 44, each having a volume of approximately 100 cubic centimeters ("cc"). The base may be molded of optically transparent medical grade plastic, such as a ABS blend that has been formulated and compounded to provide a controlled degree of flexibility in the base or housing walls. A molded retention lip around the open end of the base enables the cap 24 to snap fit to the base. Each base further includes at least one wall 64 extending substantially adjacent the sample vial for holding the sample vial in place in a predetermined position within the housing. The tension walls may be molded into the interior end walls 56, 58, the base bottom 66 or the central dividing web 46 in order to correctly position the two blood sample vials within the device.

The sample vials 48, 50 in the present invention are formed as square or rectangular cross-section thin-walled plastic friable plastic tubes or vials having an enclosed lower end 68 and an open upper end 70. Each vial is configured to hold a predetermined quantity of blood. The exterior wall of each of these vials has a molded and continuous groove feature 60, 62 that circumscribes a defined area 72 of the wall and reduces the wall thickness of the tube in the region underlining the groove. A molded-in pin or fin 52, 54 projects from the approximate center of the circumscribed or break-away area 72. The break-away area 72 preferably has dimensions of one or two inches across such that when the sample vials are properly installed in or about the base cups, the pins mate with corresponding features molded in the end walls 56, 58 of the base. The sample vials are molded of an optically transparent medical grade polymer, such as polystyrene that has been formulated and compounded such that the resulting part is both rigid and brittle. The break window 72 on the friable plastic vials 48, 50 may be broken to allow blood to communicate and flow into the first and second chambers 42, 44.

The cap 24 is comprised of molded plastic and is made of the same material as the base. The cap incorporates molded-in features that mate with the cap for retaining the cap in or on the base, so as to isolate blood and growth media within the device from contaminants of the external environment. Further, the cap is structured to captivate and compress the gasket 30 in selected areas around the perimeter of the housing. The aperture 34 molded into the cap accepts and retains the septum 40. The aperture may further incorporate precision metering orifices that communicate between the aperture and the fluid entry zones of two duck bill valves 74, 76 that feed into the sample vials, as will be subsequently discussed.

The gasket 30 is molded of a medical grade elastomer, such as silicon rubber, having a controlled durometer. At least one pair of one-way valves 74, 76 of the "duck bill" configuration are molded into the gasket. Accordingly, when the gasket is compressed and assembled to the base 22 and sample vials 48, 50, one duck bill is aligned with the open end 70 of each sample vial respectively. These duck bill valves 74, 76 are oriented to allow unidirectional fluid to flow into each sample vial and are designed to actuate at a relatively low differential pressure.

Means may also be provided to relieve or release gas pressure that builds up in the culture chambers cups during testing. Such means may take the form of any of a number of valves or ports well known to those skilled in the art, including but not limited to a second pair of duck bill valves (not shown) incorporated into the gasket, each aligned with a culture chamber compartment. These second valves would be oriented to allow gas flow from the culture chamber into the cap and may be referred to as reverse duck bill valves. These reverse duck bill valves would be designed to actuate at a differential pressure that is substantially higher than any pressure reasonably expected during normal device storage or use, but substantially less than the burst pressure of the housing of the device. Alternatively, in lieu of a duck bill valve communicating between the culture chambers and the upper compartments or upper chambers of the cap, the simply elastomeric nature of the gasket may allow for a bulge to increase the pressure within the cap. At the same time, however, the movement of the gasket should be controlled in order to allow for accurate measurements of pressure change.

When the device is assembled, the gasket is captivated and compressed between features incorporated into the cap and the upper, open ends 70 of the sample vials, so that the insides of the sample vials 48, 50 are wholly isolated from the remaining space of the culture chambers 42, 44. In this regard, the cap preferably includes an internal wall 78, 80 that presses the gasket against the sample vials and substantially isolates the filling well 32 from the other compartments 82, 84 of the cap and in turn tom the culture chambers 42, 44 of the base. The above-mentioned reverse duck bill valves or other pressure relief means may be placed either in the gasket or in this upper internal wall so that pressure build up that is unexpected may allow gas to escape through the reverse duck bill valve and through vent holes (not shown) in the cap, thus preventing a rupture in the device.

The septum 40 is manufactured of a medical grade elastomer. The septum is designed to allow fluid access to the aperture 34 and filling well 32 in the cap when penetrated by a standard hypodermic needle 86 and to seal both gas and air from either entering or leaving the device after the hypodermic needle is withdrawn.

The device of the present invention may be assembled by installing two sample vials into the base and a septum into the cap. An appropriate volume, typically on the order of about 90 cc, of an aerobic growth medium may be hot-filled into the first culture chamber 42, and a appropriate volume, also typically on the order of about 90 cc, of an anaerobic growth medium may be hot-filled into the second culture chamber 44. The culture chambers may be manufactured to be a smaller or larger size as required by different media. Alternatively, a volume-occupying block may be inserted into one of the base cups to fill up the space that would otherwise be filled with media. The media may be then filled to an appropriate mark on the wall of the housing.

Before the device and media have cooled significantly, the gasket 30 may be inserted into the top of the base and the cap snapped into place. In this way, a hermetic seal will be effected between the various compartments of the device. As the device and media cool, the fluids and the corresponding head spaces in the cap and above the media in the culture chambers contract, thus resulting in the formation of a vacuum in the culture chambers and in the sample vials. During the cooling, differential pressure forms across the duck bill valves 74, 76 that communicate with the sample vials. This causes the valves 74, 76 to crack, thereby allowing the pressure to equalize between the two sample vials, while allowing a vacuum to be drawn in the cap 24 as well. The valves 74, 76 automatically close when the pressure in these zones are approximately equalized. The device is now ready for use.

In normal practice, approximately 10 cc of blood is required to perform a single blood culture test in many applications. Since the device of the present invention performs two tests simultaneously from a single blood sample, a blood sample of, for example, 20 cc should be drawn from the patient using a hypodermic syringe. Alternatively, the required blood sample could be obtained from an in-dwelling catheter or other appropriate device. For purposes of illustration, a single hypodermic syringe is assumed to be used for the present description.

When the hypodermic syringe needle is inserted through the septum 40 and into the aperture 32, the vacuum in the filling well 32 and the aperture 34 draws out blood from the syringe into the filling well 32. This increased pressure in the well 32 causes the duck bill valves 74, 76 leading into the sample vials 48, 50 to actuate. The vacuum in the sample vials causes blood to flow from the syringe into the aperture 34 and in turn through the metering orifices and duck bill valves, into the sample vials. The sample vials preferably have identical volumes and the vacuums of each have been equalized during manufacturing. Further, the flow characteristics of the metering orifices are precisely matched and both fluid paths feed from the common source of the aperture 32. As a result, the blood sample being drawn from the syringe is approximately equally divided between the two sample vials. When the sample vials have been filled, the pressure differentials across the duck bill valves substantially approach zero, thereby allowing the duck bill valves to reseal. Upon removal of the syringe needle from the septum 40, the device is ready for activation.

The device is activated by manipulating the end walls 56, 58 of the base cups, which are preferably somewhat flexible. The motion of the outside walls communicates to the sample vials via the attached pins 52, 54. The compression of the walls 56, 58 toward each other causes the brittle sample vial walls to break along the molded-in score lines 60, 62. As a result, the blood sample in the sample vials is released into the surrounding growth media. The blood in the first vial is thus transferred to the first chamber 42, while the blood from the second vial is thus transferred to the second chamber 44. In this regard, the internal walls 46, 78, 80 of the device substantially prevent the contents of the first and second chambers 42, 44 from communicating with one another. The sample vials are designed to drain completely into the respective growth media when the sample vial walls are broken. Complete draining and mixing of blood and growth medium can be ensured, however, by gently shaking or inverting the activated device. Because the device has transparent walls, proper activation, draining and mixing can be confirmed by visually inspecting the contents.

After activation, the device can be placed in an incubator to allow any bacterial or microorganisms that may be present in the sample to grow. Growth of microorganisms can be monitored through the container's transparent walls. Additionally, pressure changes can be non-invasively monitored if the incubator preloads the device against a pair of load cells, one bearing against the side wall of each base cup compartment. Alternatively, because the walls are transparent, a healthcare technician may optically monitor gas deflection of the gasket into the upper chambers of the cap.

As the pressure within the device compartment changes, the deflection of the semi-flexible compartment wall changes and is sensed by the corresponding load cell. Still alternatively, the wall of the device may include a bellows sensor 88, which inflates outwardly through the wall as pressure inside the chamber increases. See FIGS. 1 and 2. Such a device is disclosed, for example, in U.S. Pat. No. 5,051,360 (Waters).

Any or all of the accessible parameters can be monitored, as desired, throughout the period of incubation, and the resulting signals can be analyzed to detect and characterize any changes that may take place. The changes due to microorganism growth are distinctive and can be resolved from perturbing factors, such as temperature and barometric pressure changes. When the test is completed, the device is removed from the incubator, and the device is autoclaved and properly discarded.

If, during incubation or autoclaving, excess pressure develops in the device, the duck bill valves that communicate between the base cup compartments and the cap will open. This allows the excess pressure to vent through a fluid trapping feature in the cap and in turn to the external ambient environment. The fluid trap prevents fluid and aerosols from being released during venting and as a result of unexpectedly high pressure build up.

Figure 5:
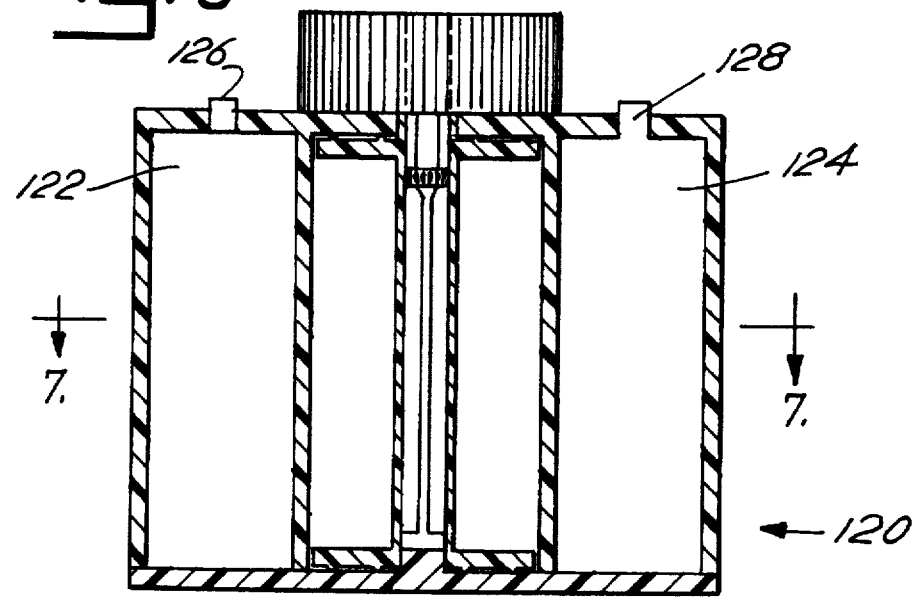
FIG. 5 is a cross-sectional view of the device shown in FIG. 4.

Referring to FIGS. 4 and 5, an alternative embodiment of the present invention is shown as a blood culture device 120 having first and second blood culture chambers 122, 124 as well as an internal blood valve assembly. Each blood culture chamber may be filled with an appropriate growth medium through ports 126, 128. As illustrated in FIGS. 6–8, the valve assembly includes an arrangement of partition walls 130–136 designed to rotate about a central blood inlet 138 and within curved fixed walls 140, 142, to thereby provide first and second blood vial compartments 144, 146 which are isolated from each other. When in a loading position as illustrated in FIG. 6, the blood vial compartments 144, 146 are isolated from the culture chambers 122, 124, and blood may flow from the blood inlet 138 into the blood vial compartments. Upon rotation, for example by knob 125, to a sealed position as illustrated in FIG. 7, the blood vial compartments are isolated from the blood inlet as well as from the culture chambers. Finally, upon rotation to an activation position as illustrated in FIG. 8, the blood vial compartments are opened to communicate with the culture chambers, and blood mixes with the respective test media. In this embodinmnt, the movable partition walls 130–136 must form a tight seal against the curved fixed walls 140, 142, in order to isolate the blood from the blood culture chambers until the device is turned to the activation position as depicted in FIG. 8. Finally, ports 126, 128 can alternatively be used for sensing purposes, including a bellows sensor as described above.

FIG. 9 discloses another alternative embodiment of the present invention. This embodiment requires only a single blood vial 222 for holding a sample of blood, and incorporates a dual-piston or dual shuttle valve assembly 224. As illustrated, both pistons may be displaced upwardly inside the cylinder to thereby draw blood from first and second blood vial ports 226, 228 into the metering chamber or shuttle chamber. Thereafter, the blood pistons may move downwardly so as to press the blood that has entered the shuttle chamber through output ports 230, 232 and into first and second culture vials (not shown). Directional duck bill valves or can further be incorporated to prevent blood from reentering the vial and thereby to require the blood to flow into the cultured vials.

Figure 10B:
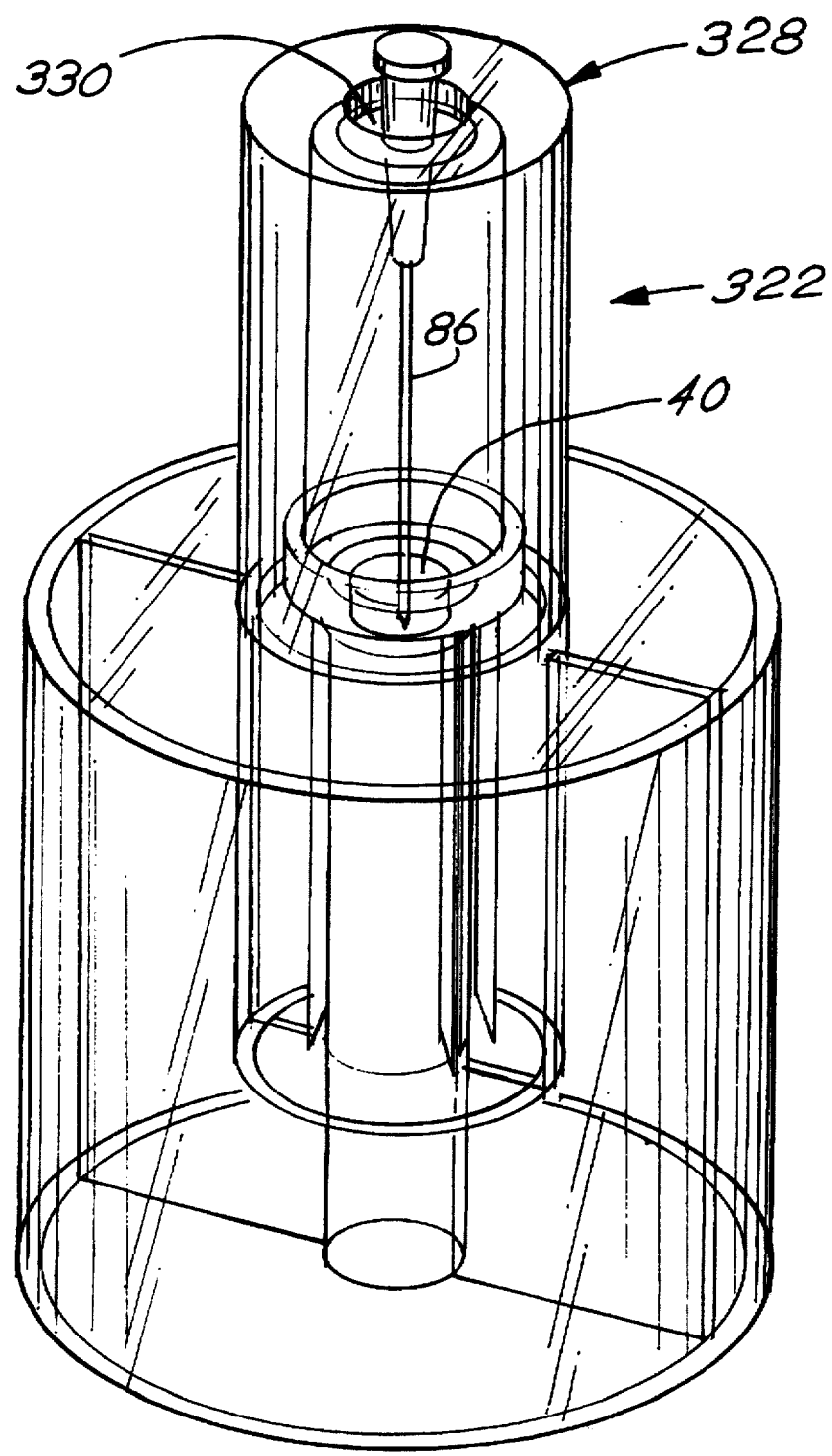
Figure 10D:
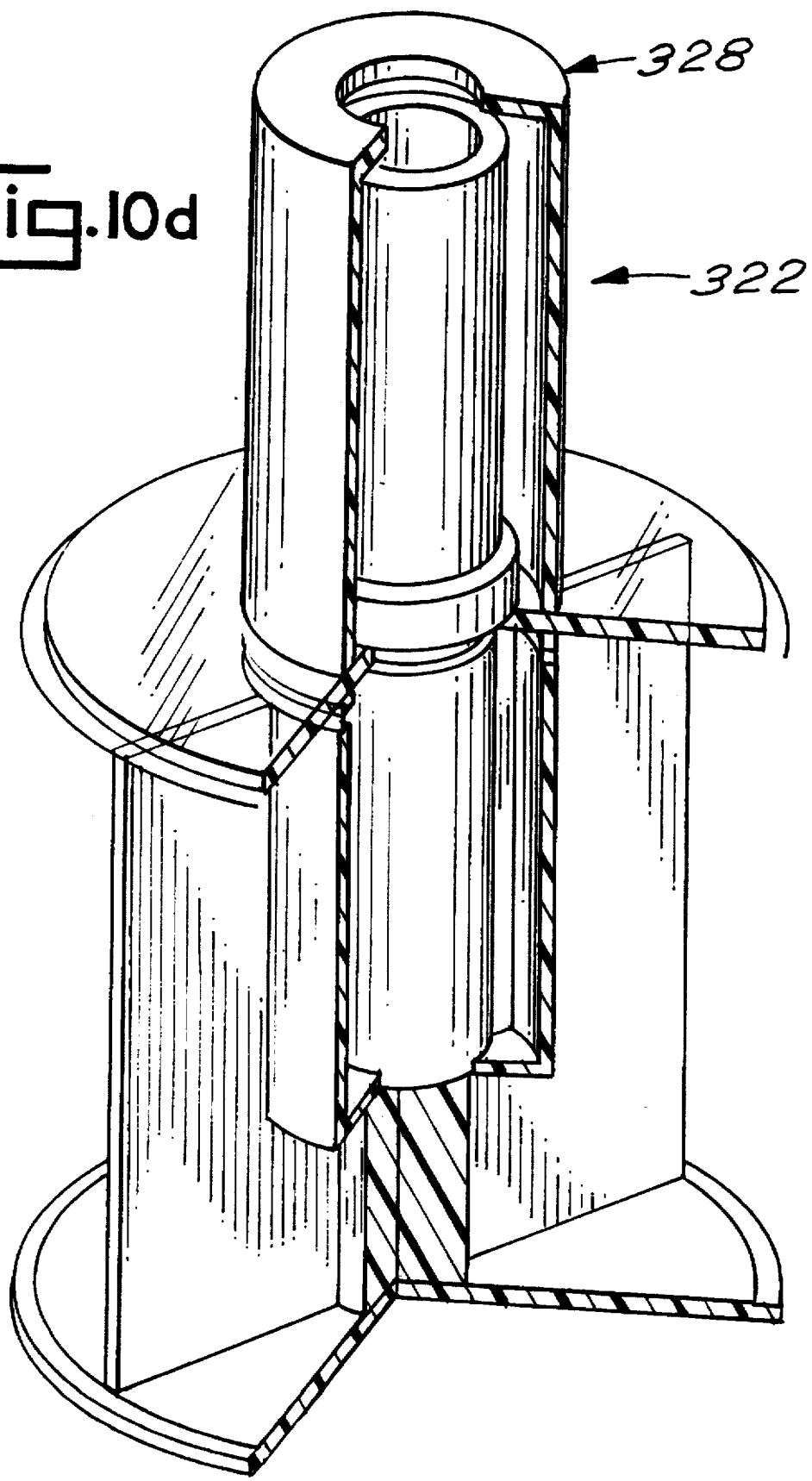

FIG. 10 illustrates yet another alternative embodiment of the present invention. In this embodiment, a configuration is provided for integrally holding and capturing the specimen syringe and/or specimen needle in the blood culture apparatus. This configuration eliminates the need to separately discard the syringe and/or needle after testing. In this embodiment, a supplemental needle chamber 322 extends outwardly from the septum 40 or input port of the device. The supplemental needle chamber has a hollow core 324 defined by internal walls 326. The end 328 of the supplemental chamber 322 opposite the septum 40 bears a capture disk 330 configured to be penetrated by, and to integrally hold, the specimen needle 86, which in turn preferably penetrates the septum 40. In use, a blood specimen is then injected through the supplemental chamber 322 and into the sample compartments (e.g., 48, 50) of the blood culture device, while any overflow of blood is preferably captured by the supplemental chamber. Upon completion of testing, the integrally attached blood culture container and specimen needle are appropriately disposed of as one single unit. Further modified, it is contemplated that this embodiment may also capture substantially all of the syringe and needle in the supplemental chamber, for instance by means of an extension or syringe port 332 (shown in shadow) of the supplemental chamber 322.

Figure 11:
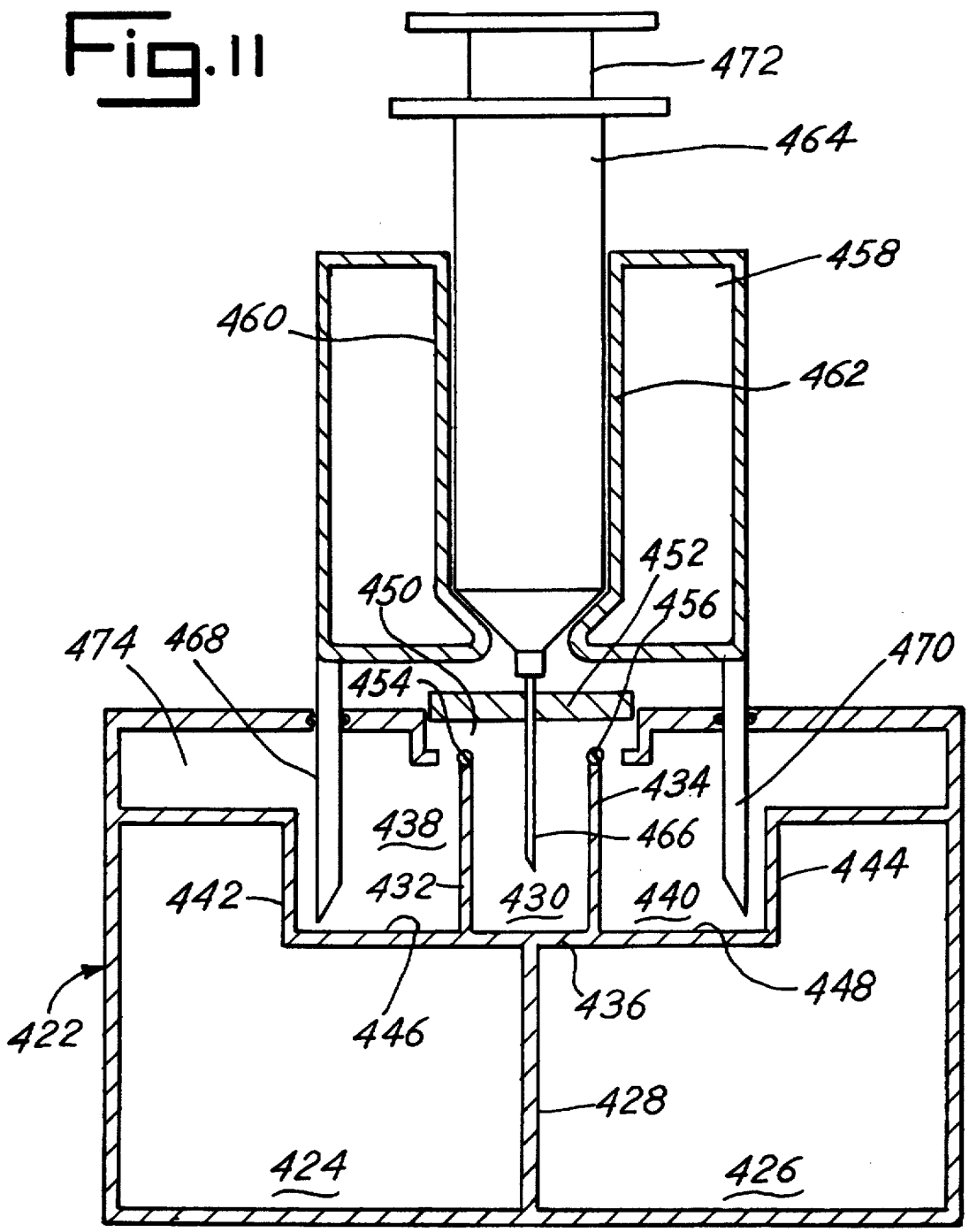
FIG. 11 is a cross-sectional view of still another embodiment of the present invention, providing alternative means to capture the specimen syringe.

FIGS. 11 and 12 illustrate still another embodiment of the present invention, providing alternative means for capturing the specimen syringe with a dual chamber blood culture apparatus. In this embodiment, the base 422 includes two enclosed blood culture chambers 424, 426, separated by a central wall 428. The blood culture chambers 424, 426 are filled with appropriate growth media, for example, as described above. A central specimen receiving compartment or inlet 430, defined by compartment walls 432–436, is positioned above the central wall 428. Juxtaposed on both sides of the central specimen receiving compartment are sample compartments 438, 440 defined by a combination of the compartment walls 432, 434, outer walls 442, 444 and compartment floors 446, 448.

An opening 450 in the blood culture apparatus is provided above the central receiving compartment 430. The opening is configured to hold a septum 452 having at least two positions, an opened state and a closed state. In the opened state, the septum 452 allows fluid communication over the compartment walls 432, 434 between the central receiving compartment 430 and the sample compartments 438, 440. In the closed state, the septum 452 is pressed against the tops 454, 456 of the compartment walls 432, 434, thus separately sealing closed the central receiving compartment 430 and the sample compartments 438, 440.

A syringe port 458 is provided over the septum 452. The syringe port 458 includes walls 460, 462 for holding the specimen syringe 464 and is configured to allow the specimen needle 466 to penetrate the septum 452 and enter the central receiving compartment 430. It is contemplated that the walls 460, 462 may be shaped to correspond to the shape of the syringe, however those skilled in the art would appreciate that various alternative shapes are possible. Connected to the shaped walls 460, 462 of the syringe port 458 are pins 468, 470, which protrude into the sample compartments 438, 440 for activation purposes as will be described.

In use, the syringe 464 is inserted into the syringe port 458 and the needle 466 is thereby inserted through the septum 452 and into the central receiving compartment 430. The syringe plunger 472 is applied, to inject blood from the syringe 464 into the central receiving compartment 430. Once the central receiving compartment 430 fills with blood, the blood overflows in substantially equal quantities into the sample compartments 438, 440. Excess blood may flow into appropriately positioned overflow chambers 74, 476 above the blood culture chambers 424, 426. Once the sample compartments 438, 440 have been filled, the syringe 464 is pressed further down, pushing the septum 452 down into its closed state. Any of a variety of locking means may also be provided to then lock the syringe 464 into the syringe port 458. By next pressing down on the syringe port 458, the pins 468, 470 protruding from the walls of the syringe port 458 into the sample compartments 438, 440 are moved downwardly and thereby breach the floors 446, 448 of the sample compartments 438, 440. As a result, the blood in the sample compartments 438, 440 flows into respective blood culture chambers 424, 426 for testing. Upon completion of testing, the integral combination of the blood culture apparatus and the syringe may be appropriately disposed of.

In addition, it is contemplated that the alternative embodiment of FIG. 11 can also include a threaded actuating cap disposed about the syringe port. As illustrated in FIG. 12, the actuating cap 478 bears threads 480, which correspond to threads disposed about the syringe port. The actuating cap is designed to push the syringe port 458 down when activation of the blood culture test is desired. Thus, once the contents of the syringe 464 have been emptied into the central receiving compartment 430 and sample compartments 438, 440, the actuating cap 478 can be turned, for instance, one quarter turn, in order to displace the pins 468, 470 downwardly through the floors 446, 448 of the sample compartments 438, 440 and commence testing.

Still another embodiment of the present invention is shown in FIGS. 13 through 16. This embodiment also incorporates means to capture the specimen syringe. As illustrated, this embodiment includes a base 520 divided by a central wall 522 into two media compartments 524, 526. Each media compartment 524, 526 contains an appropriate growth medium, such as an aerobic or anaerobic medium. Centrally positioned above the central wall 522 is a specimen inlet 528, also referred to as a central blood receiving inlet, including a syringe port 530 configured to receive a syringe 532, a set of pistons 534, 536 also referred to as a piston assembly, and at least two sample cups or sample containers 538, 540. As the syringe 532 is pushed down into the inlet 528, blood from the syringe 532 can be inserted into the sample cups 538, 540 through fill ports 542, 544 as will now be described.

As shown in FIG. 13, the specimen syringe 532 is first inserted into the syringe port 530 in a slide defined by walls 546, 548. In this state, the fill ports 542, 544 are closed at the bases 546, 548 of the sample cups 538, 540. Turning to FIG. 14, the syringe 532 is pushed further into the inlet 528, and, as the pistons 534, 536 are thereby drawn upwardly, blood is drawn from the needle 550, through the fill ports 542, 544 and into the sample cups 538, 540. Notably, while the figures illustrate one piston assembly configuration, those skilled in the art would appreciate that numerous alternative configurations can be substituted to draw blood into the specimen inlet 528 and in turn into sample cups 538, 540.

Next, as shown in FIG. 15, the syringe 532 is pushed still further into the inlet 528, and the sample cups 538, 540 are thereby pushed further down, so that the fill ports 542, 544 once again reach a closed state, this time at the tops 552, 554 of the sample cups 538, 540. Finally, as shown in FIG. 16, the syringe 532 is pushed substantially completely down into the inlet 528. Locking means are preferably provided to lock the syringe 532 in place within the specimen inlet. These locking means can include a latch or detents about the inner edges of the syringe port or, alternatively, any of a multitude of other locking configurations well known to those skilled in the art. As the syringe 532 is thus pushed down, the sample cups 538, 540 are released from the specimen inlet 528 into the respective media compartments 524, 526 and blood is released from the sample cups 538, 540 in order to initiate blood culture testing. Again, upon completion of testing, the single integral device, including the blood culture apparatus and the syringe, can be appropriately disposed of.

Various embodiments of the present invention have been described above. Those skilled in the art will understand, however, that changes and modifications may be made in these embodiments without departing from the true scope and spirit of the present invention, which is defined by the following claims.

We claim:

1. A multi-chamber blood culture apparatus integrally comprising, in combination:

a base for receiving at least two different growth media, said base having outer walls defining first and second culture chambers for containing, respectively, first and second growth media and for receiving first and second predetermined quantities of blood, said first and second culture chambers holding, respectively, an aerobic growth medium and an anaerobic growth medium, said outer wall being comprised of substantially optically transparent plastic, whereby growth of microorganisms within said growth media may be visually observed, and whereby fluorescence and optical absorbance of said microorganisms may be observed;

first and second sample containers comprised of friable plastic material and supported by said base, said first culture chamber fixedly carrying said first sample container for receiving and holding said first predetermined quantity of blood, and said second culture chamber fixedly carrying said second sample container for receiving and holding said second predetermined quantity of blood;

a cap adjacent to said base and said sample containers for isolating said blood and growth media within said apparatus from an external environment, said cap including a filling well containing orifices for communicating blood from a syringe to said sample containers;

a gasket substantially between said cap and said base and sample containers, said gasket including at least first and second duck bill valves communicating, respectively, with said first and second sample containers to allow unidirectional flow of blood from said filling well into said sample containers;

said cap defining first and second upper chambers adjacent said first and second culture chambers, said gasket separating said first and second upper chambers from said first and second culture chambers;

first and second pins, said first pin communicating between said first sample container and said outer wall, and said second pin communicating between said second sample container and said outer wall, each of said sample containers bearing a break-away portion, whereby pressing said outer walls drives said pins into said sample containers so as to allow blood from said first sample container to combine with said first growth media and blood from said second sample container to combine with said second growth media; and a bellows sensor within said outer wall for measuring pressure change within at least one of said culture chambers.

2. A multi-chamber blood culture apparatus integrally comprising, in combination:

means for separately holding at least two different growth media;

means for receiving a blood specimen into at least two separate sample containers; and means for releasing said blood specimen from said two separate sample containers to respectively combine with said two different growth media.

3. A multi-chamber blood culture device integrally comprising, in combination:

an apparatus as claimed in claim 2; and syringe capture means for integrally capturing a specimen syringe together with said apparatus, such that said specimen syringe and said apparatus become one single disposable unit.

4. A multi-chamber blood culture apparatus integrally comprising, in combination:

a base having outer walls defining first and second culture chambers for containing, respectively, first and second growth media and for receiving first and second predetermined quantities of blood, said first and second culture chambers holding, respectively, an aerobic growth medium and an anaerobic growth medium, said outer wall being comprised of substantially optically transparent plastic, whereby growth of microorganisms within said growth media may be visually observed, and whereby fluorescence and optical absorbance of said microorganisms may be observed;

first and second sample containers comprised of friable plastic material and supported by said base, said first culture chamber fixedly carrying said first sample container for receiving and holding said first predetermined quantity of blood, and said second culture chamber fixedly carrying said second sample container for receiving and holding said second predetermined quantity of blood;

a cap adjacent to said base and said sample containers for isolating said blood and growth media within said apparatus from an external environment, said cap including a septum and a filling well containing orifices for communicating blood from a syringe to said sample containers;

a gasket substantially between said cap and said base and sample containers, said gasket including at least first and second duck bill valves communicating, respectively, with said first and second sample containers to allow unidirectional flow of blood from said filling well into said sample containers;

said cap defining first and second upper chambers adjacent said first and second culture chambers, said gasket separating said first and second upper chambers from said first and second culture chambers;

first and second pins, said first pin communicating between said first sample container and said outer wall, and said second pin communicating between said second sample container and said outer wall, each of said sample containers bearing a break-away portion, whereby pressing said outer walls drives said pins into said sample containers so as to allow blood from said first sample container to combine with said first growth media and blood from said second sample container to combine with said second growth media; and capture means for integrally capturing a needle of said syringe, such that said needle and said apparatus become a single unit.

5. An apparatus as claimed in claim 4 wherein said capture means includes a supplemental needle chamber for capturing said needle, said supplemental needle chamber extending outwardly from said septum and comprising:

a hollow core defined by internal walls; and a capture disk for receiving and integrally holding said needle in said hollow core while enabling said needle to penetrate said septum for injection of blood into said filling well.

6. An apparatus as claimed in claim 5 further including means for integrally capturing said syringe, such that said syringe and said apparatus become a single disposable unit.

7. A multi-chamber blood culture apparatus comprising, in combination:

at least one sample container for holding a predetermined quantity of blood;

at least a pair of culture chambers for holding at least two different growth media and for receiving said blood from said at least one sample container;

a dual shuttle valve assembly interconnecting said at least one sample container and said culture chambers, said dual shuttle valve assembly having (i) first and second outlet ports, (i) first and second shuttle chambers substantially isolated from each other and (ii) two interconnected pistons configured to move in unison for substantially simultaneously drawing out first and second predetermined quantity of blood from said at least one sample vial and for substantially delivering said first predetermined quantity of blood through said first outlet port to said first culture chamber and said second predetermined quantity of blood through said second outlet port to said second culture chamber.

8. An apparatus as claimed in claim 7 further comprising a cover adjacent said at least one sample container and said culture chambers for isolating said blood and growth media within said apparatus from outside contaminants.

9. A multi-chamber blood culture apparatus integrally comprising, in combination:

a base having outer walls defining first and second culture chambers for containing, respectively, first and second growth media and for receiving first and second predetermined quantities of blood;

first and second sample containers supported by said base for containing, respectively, said first and second predetermined quantities of blood, said first and second predetermined quantities of blood being separated from said first and second growth media;

means for isolating said blood and growth media within said apparatus from an external environment; and first and second pins communicating respectively between said outer walls and said sample containers for conveying pressure from said outer walls to said sample containers to thereby release said blood from said sample containers into said culture chambers.

10. An apparatus as claimed in claim 9 further comprising means for communicating blood from a syringe to said sample containers.

11. An apparatus as claimed in claim 10, wherein said means for isolating said blood and growth media within said apparatus from an external environment comprises a cap adjacent to said base and said sample containers, and wherein said means for communicating blood from a syringe to said sample containers comprises a filling well in said cap, said filling well containing orifices for communicating blood from a syringe to said sample containers.

12. An apparatus as claimed in claim 11, wherein said filling well overhangs said sample containers and wherein substantially equivalent orifices overhang each of said sample containers, whereby substantially equal quantities of blood are delivered to said first and second sample containers.

13. An apparatus as claimed in claim 9, wherein said first culture chamber fixedly carries said first sample container and said second culture chamber fixedly carries said second sample container.

14. An apparatus as claimed in claim 9, wherein said first growth medium is aerobic and said second growth medium is anaerobic.

15. An apparatus as claimed in claim 9, wherein said means for isolating said blood and growth media within said apparatus from an external environment comprises a cap adjacent to said base and said sample containers.

16. An apparatus as claimed in claim 15, further comprising a septum within said cap, whereby a needle from a syringe may be inserted through said septum for delivery of blood to said sample containers.

17. An apparatus as claimed in claim 15, further comprising a gasket substantially between said cap and said base and sample containers.

18. An apparatus as claimed in claim 17, wherein said gasket includes first and second valves communicating, respectively, with said first and second sample containers to allow unidirectional flow of blood from said filling well into said sample containers.

19. An apparatus as claimed in claim 17, wherein said cap defines first and second upper chambers adjacent said first and second culture chambers and said gasket separates said first and second upper chambers from said first and second culture chambers.

20. An apparatus as claimed in claim 9, wherein said first and second sample containers are comprised of friable plastic material.

21. An apparatus as claimed in claim 9, wherein said first pin communicates between said first sample container and said outer wall, and said second pin communicates between said second sample container and said outer wall, whereby pressing said outer walls drives said pins into said sample containers so as to allow blood from said first sample container to combine with said first growth media and blood from said second sample container to combine with said second growth media.

22. An apparatus as claimed in claim 21, wherein said first and second sample containers bear break-away portions, whereby pressing on said outer walls drives said pins into said break-away portions.

23. An apparatus as claimed in claim 9, wherein said outer wall is comprised of substantially optically transparent plastic, whereby growth of microorganisms within said growth media may be visually observed, and whereby fluorescence and optical absorbance of said microorganisms may be observed.

24. An apparatus as claimed in claim 9, further comprising a membrane within said outer wall configured to expand under increased pressure within at least one of said culture chambers.

25. An apparatus as claimed in claim 9, further comprising a bellows sensor within said outer wall for measuring pressure change within at least one of said culture chambers.

26. An apparatus as claimed in claim 9, further including means for integrally capturing said syringe, such that said syringe and said apparatus become a single disposable unit.

* * * * *